(12) United States Patent
Brown et al.

(10) Patent No.: US 9,697,996 B2
(45) Date of Patent: Jul. 4, 2017

(54) DDA EXPERIMENT WITH REDUCED DATA PROCESSING

(71) Applicant: Micromass UK Limited, Wilmslow (GB)

(72) Inventors: Jeffery Mark Brown, Hyde (GB); Kevin Giles, Stockport (GB); Martin Raymond Green, Bowdon (GB); John Brian Hoyes, Stockport (GB); Christopher Jones, Macclesfield (GB); Michael Raymond Morris, Derbyshire (GB); Steven Derek Pringle, Darwen (GB); Keith Richardson, Derbyshire (GB); Farnoush Salarzaei, Cheshire (GB); Jason Lee Wildgoose, Stockport (GB)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 14/774,756

(22) PCT Filed: Mar. 10, 2014

(86) PCT No.: PCT/GB2014/050697
§ 371 (c)(1),
(2) Date: Sep. 11, 2015

(87) PCT Pub. No.: WO2014/140542
PCT Pub. Date: Sep. 18, 2014

(65) Prior Publication Data
US 2016/0035548 A1    Feb. 4, 2016

(30) Foreign Application Priority Data

Mar. 13, 2013 (EP) ..................................... 13159080
Mar. 13, 2013 (GB) ................................... 1304536.4

(51) Int. Cl.
H01J 49/00       (2006.01)
G01N 27/62       (2006.01)

(52) U.S. Cl.
CPC ........ H01J 49/005 (2013.01); H01J 49/0031 (2013.01); H01J 49/0045 (2013.01); H01J 49/0072 (2013.01); G01N 27/622 (2013.01)

(58) Field of Classification Search
USPC ................................................. 250/281, 282
See application file for complete search history.

(56) References Cited

U.S. PATENT DOCUMENTS 6,906,319 B2 *  6/2005  Hoyes ................... H01J 49/004
                                                         250/281
7,095,014 B2     8/2006  Hoyes
(Continued)

FOREIGN PATENT DOCUMENTS

GB            2389704        6/2004

OTHER PUBLICATIONS

Haller et al., "Collision Induced Decomposition of Peptides. Choice of Collision Parameters", Journal of the American Society for Mass Spectrometry, pp. 677-681, 1996.

Primary Examiner — Kiet T Nguyen
(74) Attorney, Agent, or Firm — Diederiks & Whitelaw, PLC

(57) ABSTRACT

A method of mass spectrometry is disclosed comprising: performing a survey scan of a plurality of different types of parent or precursor ions, wherein the survey scan comprises analyzing the ion mobilities of the ions and mass analyzing the ions; determining the charge states of parent or precursor ions analyzed in the survey scan based on their determined combinations of ion mobility and mass to charge ratio; selecting a parent or precursor ion for fragmentation or reaction; and fragmenting or reacting the selected ion, wherein the fragmentation or reaction conditions are (Continued)

selected from a plurality of different fragmentation or reaction conditions based upon the determined charge state of the selected ion.

25 Claims, 1 Drawing Sheet

(56) References Cited

U.S. PATENT DOCUMENTS

| | | |
|---|---|---|
| 7,586,088 B2 | 9/2009 | Bateman et al. |
| 7,622,711 B2 | 11/2009 | Wildgoose et al. |
| 8,168,943 B2 | 5/2012 | Schwartz et al. |
| 8,278,620 B2 | 10/2012 | Schwartz et al. |
| 8,921,773 B2 | 12/2014 | Geromanos et al. |
| 2010/0108879 A1 | 5/2010 | Bateman et al. |
| 2011/0057098 A1* | 3/2011 | Le Blanc ............ H01J 49/4295 250/283 |

* cited by examiner

DDA EXPERIMENT WITH REDUCED DATA PROCESSING

CROSS-REFERENCE TO RELATED APPLICATION

This application is the National Stage of International Application No. PCT/GB2014/050697, filed 10 Mar. 2014 which claims priority from and the benefit of United Kingdom patent application No. 1304536.4 filed on 13 Mar. 2013 and European patent application No. 13159080.4 filed on 13 Mar. 2013. The entire contents of these applications are incorporated herein by reference.

BACKGROUND OF THE PRESENT INVENTION

The present invention relates to a method of mass spectrometry and a mass spectrometer.

Data Directed Acquisition ("DDA") modes of operation are known in mass spectrometry. In such a mode, mass spectral data of parent or precursor ions is initially acquired in a MS mode. The mass spectral data is then processed to determine candidate parent or precursor ions of interest, from which it is subsequently desired to obtain MS/MS data from. Each candidate parent or precursor ion is then sequentially selected and MS/MS analysis is performed on each candidate parent or precursor ion of interest in turn.

The criteria for switching to MS/MS analysis can be quite complicated and may involve include and exclude lists, adducts and losses etc, i.e. "chemical intelligence". With recent increases in performance of chromatography separation, ever greater demands are being placed upon the mass spectrometer. In particular, it is desired to increase the number of MS/MS switches whilst maintaining as high a duty cycle as possible.

The desire to increase the performance or duty cycle of mass spectrometers performing Data Directed Analysis ("DDA") places increased requirements on the mass spectrometer in terms of the time taken to process the initial survey spectrum. However, increasing the time spent processing survey spectra of parent or precursor ions increases the "dead time" of the instrument, i.e. the time when the instrument is not collecting data.

It is therefore desired to provide an improved mass spectrometer and method of mass spectrometry.

SUMMARY OF THE PRESENT INVENTION

According to an aspect of the present invention there is provided a method of mass spectrometry comprising:

performing a survey scan of a plurality of different types of parent or precursor ions, wherein said survey scan comprises analyzing the ion mobilities of the ions and mass analyzing the ions;

determining the charge states of parent or precursor ions analyzed in the survey scan based on their determined combinations of ion mobility and mass to charge ratio;

selecting a parent or precursor ion for fragmentation or reaction; and fragmenting or reacting said selected ion, wherein the fragmentation or reaction conditions are selected from a plurality of different fragmentation or reaction conditions based upon the determined charge state of the selected ion.

As the survey scan in the present invention separates the parent or precursor ions by ion mobility and also mass analyzes the ions, the survey scan is able to determine the charge states of the ions and hence determine which ions are of interest. As the survey scan determines the charge states of the ions, this reduces the subsequent processing conventionally required in order to identify the ions of interest. The present invention therefore reduces the "dead time" of the instrument. Also, as the survey scan of the present invention identifies the charge states of the ions, it is able to use this data to simultaneously optimise the fragmentation or reaction conditions in the MS/MS mode of operation, thereby improving the spectral data obtained for the product or fragment ions and hence improving the sensitivity of the instrument and ability to identify the parent or precursor ions.

It is known to selectively transmit ions having a predetermined combination of mass to charge ratio and ion mobility in order to isolate ions of a desired charge state. For example, GB 2443952 discloses the use of a mass filter to transmit ions having a specific mass to charge ratio to an ion mobility separator, in which the ions are separated according to their ion mobility. An ion gate is provided at the exit of the ion mobility separator and is synchronised therewith such that only ions having a particular mass to charge ratio and charge state are onwardly transmitted.

However, it is not known to perform a survey scan in a DDA experiment that determines the charge state of the parent or precursor ions in the MS mode, or to optimise the fragmentation or reaction conditions in the MS/MS mode based on the determined charge states. The prior art merely identifies that charge states can be selected, but does not recognise the importance of determining the charge states in a survey scan of a DDA experiment so as to reduce "dead time" and optimise the MS/MS mode of operation.

Preferably, the step of determining the charge states of the ions is part of the survey scan.

The method of mass spectrometry is preferably a method of data dependent acquisition (DDA) mass spectrometry. The survey scan is preferably a MS scan and the steps of selecting and fragmenting or reacting the ions are preferably part of an MS/MS scan.

Said step of selecting a parent or precursor ion for fragmentation or reaction preferably comprises selecting a parent or precursor ion based on its determined charge state.

The method preferably comprises sequentially selecting and fragmenting or reacting different parent or precursor ions. Preferably, one parent or precursor ion is selected and isolated at a time. This may be achieved, for example, by using a mass filter (and optionally an ion mobility separator) so as to transmit only ions having the desired mass to charge ratio (and optionally also the desired ion mobility).

Preferably, any given selected ion is isolated from other ions before being subjected to said fragmentation or reaction.

The method may comprise selecting the optimum fragmentation or reaction condition for the selected ion based upon the determined charge state of the ion.

Alternatively, or additionally, the step of fragmenting or reacting said ion may comprise fragmenting said ion, and the fragmentation energy with which the ion is fragmented may be selected based upon the determined charge state of the selected ion.

The step of fragmenting or reacting the ion may comprise fragmenting said ions by Collision Induced Dissociation ("CID"), and the collision energy may be selected based upon the determined charge state of the selected ion.

The method may comprise providing means for fragmenting or reacting said ions by a plurality of different fragmentation or reaction techniques, wherein said step of selecting the fragmentation or reaction condition comprises selecting between said plurality of different types of fragmentation or reaction techniques based upon the determined charge state of the selected ion, and then fragmenting or reacting the selected ion using the selected fragmentation or reaction technique. For example, the method may select between Collision Induced Dissociation ("CID") and Electron Transfer Dissociation ("ETD"). The method may select between these fragmentation or reaction techniques and other additional techniques. Alternatively, the method may select only between techniques other than CID and ETD.

The step of selecting said fragmentation or reaction condition for said ion may comprise selecting the strength of an electric field for accelerating said selected parent or precursor ion into a Collision Induced Dissociation ("CID") region so that said selected ion enters the region with its optimal collision energy for fragmentation.

An example of a reaction condition for said parent or precursor ions is to subject said ion to a neutral reagent, such as tri(dimethylamino)borane (TDMAB), so as to rapidly derivatize N-oxide N-oxide functional group in drug metabolites.

The method preferably comprises selecting the parent or precursor ions that are to be subjected to said fragmentation or reaction based on the results of the survey scan.

Preferably, the collision energy or fragmentation condition is selected based upon the determined charge state of the parent or precursor ion and also based upon the determined mass to charge ratio value of the parent or precursor ion.

The method may comprise fragmenting or reacting a group of different ions derived from chemical compounds in the same class, wherein said different ions have different mass to charge ratios and ion mobilities, preferably wherein said class of chemical compounds corresponds to compounds that share one or more common functional group or share a common moiety, preferably, such that the one or more functional group or moiety provides the compounds with similar chemical reactivity or with a common chemical property.

Said class of compounds may be one of: lipids, pesticides; metabolites; peptides; proteins; antibodies; enzymes; a class of compounds with related biological function or activity; a class of compounds with related chemical structure; a class of compounds with related chemical reactivity; or a class of compounds with related solution chemistry.

For example, the IMS drift time may be used to identify and select just parent or precursor ions in a certain class of compounds, such as lipids or glycans, polymers such as PEG or PPG, or pharmaceuticals containing active ingredients that are reacted with polymers such as PEG to increase their "lifetime" in the body. These selected ions are then fragmented or reacted according to the present invention.

The method preferably comprises mass analyzing and/or ion mobility analyzing the fragment or product ions resulting from said fragmenting or reacting step.

The method preferably comprises associating the fragment or product ions with their respective parent or precursor ions.

The method preferably comprises identifying one or more parent or precursor ions using said analyzed product or fragment ions.

The present invention also provides a mass spectrometer comprising:
an ion mobility spectrometer;
a mass analyzer;
a fragmentation or reaction region; and
a control system arranged and adapted to:
perform a survey scan of a plurality of different types of parent or precursor ions, wherein said survey scan comprises analyzing the ion mobilities of the ions in said ion mobility spectrometer and mass analyzing the ions in said mass analyzer;
determine the charge states of the parent or precursor ions analyzed in the survey scan based on their determined combinations of ion mobility and mass to charge ratio;
select a parent or precursor ion for fragmentation or reaction in said fragmentation or reaction region;
select the fragmentation or reaction condition from a plurality of fragmentation or reaction conditions based upon the determined charge state of the selected ion; and
fragment or react said selected ion under said selected fragmentation or reaction condition in said fragmentation or reaction region.

The mass spectrometer may be arranged and configured to perform any one or combination of the preferred or optional method features described herein.

From a second aspect, the present invention provides, a method of mass spectrometry comprising:
separating ions according to their ion mobility;
mass analyzing said ions;
determining the charge state of at least some of said ions based upon the determined ion mobility and mass to charge ratio of said ions; and
determining or selecting one or more fragmentation or reaction conditions for said ions based upon the determined charge state of said ions.

The method preferably comprises performing a survey scan of a plurality of different types of parent or precursor ions, wherein said survey scan comprises said steps of separating ions according to their ion mobility and said step of mass analyzing ions.

The method preferably comprises determining or selecting one or more optimum fragmentation or reaction conditions for said ions based upon the determined charge state of said ions.

The method preferably comprises arranging a fragmentation or reaction device to operate under said one or more fragmentation or reaction conditions (e.g. optimum conditions); and fragmenting or reacting ions in said fragmentation or reaction device.

The step of determining or selecting said one or more fragmentation or reaction conditions may comprise determining or selecting an optimum collision energy for said ions.

The step of fragmenting or reacting said ions may comprise fragmenting said ions in a Collision Induced Dissociation ("CID") fragmentation device. The fragmentation or reaction condition that is determined or selected may be the collision energy in the CID device.

The step of determining or selecting said one or more fragmentation or reaction conditions may comprise determining whether or not to fragment or react said ions by Collision Induced Dissociation ("CID") or by Electron Transfer Dissociation ("ETD") or, optionally, by another fragmentation or reaction process. For example, CID fragmentation may be selected for low charge states whereas ETD fragmentation may be selected for higher charge states.

The present invention also provides a mass spectrometer comprising:
an ion mobility spectrometer;
a mass analyzer; and a control system arranged and adapted:

(i) to determine the charge state of at least some ions based upon determining the ion mobility and mass to charge ratio of said ions; and (iii) to select or determine one or more fragmentation or reaction conditions for said ions based upon the determined charge state of said ions.

The mass spectrometer may be arranged and configured to perform any one of the methods described herein.

Preferably, the mass spectrometer comprises a fragmentation or reaction device.

Preferably, said control system is arranged and adapted: (i) to cause said fragmentation or reaction device to operate under said one or more fragmentation or reaction conditions; and (ii) to cause said ions to be fragmented or reacted in said fragmentation or reaction device.

From a third aspect the present invention provides a method of mass spectrometry comprising:

performing an initial survey scan;

determining the charge state of at least some ions of interest;

determining or selecting one or more fragmentation or reaction conditions for said ions of interest based upon the determined charge state of said ions of interest;

selecting at least some of said ions of interest;

causing said selected ions of interest to fragment or react under said one or more fragmentation or reaction conditions so as to form fragment or product ions; and then mass analyzing said fragment or product ions.

The method may comprise any one or combination of features described above in relation to the first aspect of the present invention.

The method may comprise determining or selecting one or more optimum fragmentation or reaction conditions for said ions of interest based upon the determined charge state of said ions of interest.

The step of determining the charge state of at least some ions of interest preferably comprises determining the ion mobility drift time and mass to charge ratio of said ions of interest.

The step of determining or selecting said one or more fragmentation or reaction conditions for said ions of interest may comprise determining an optimum electric field to be maintained upstream of a Collision Induced Dissociation ("CID") fragmentation device so that said ions of interest are accelerated into said Collision Induced Dissociation fragmentation device with an optimal collision energy for fragmentation.

The present invention also provides a mass spectrometer comprising:

a mass or mass to charge ratio filter;

a fragmentation or reaction device;

a mass analyzer; and a control system arranged and adapted:

(i) to perform an initial survey scan;

(ii) to determine the charge state of at least some ions of interest;

(iii) to determine or select one or more fragmentation or reaction conditions for said ions of interest based upon the determined charge state of said ions of interest;

(iv) to select at least some of said ions of interest using said mass or mass to charge ratio filter;

(v) to cause said selected ions of interest to fragment or react under said one or more fragmentation or reaction conditions in said fragmentation or reaction device so as to form fragment or product ions; and then (vi) to mass analyze said fragment or product ions using said mass analyzer.

The mass spectrometer may be arranged and configured to perform any one of the methods described herein.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; and (xxi) an Impactor ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyzer selected from the group consisting of: (i) a quadrupole mass analyzer; (ii) a 2D or linear quadrupole mass analyzer; (iii) a Paul or 3D quadrupole mass analyzer; (iv) a Penning trap mass analyzer; (v) an ion trap mass analyzer; (vi) a magnetic sector mass analyzer; (vii) Ion Cyclotron Resonance ("ICR") mass analyzer; (viii) a Fourier Transform Ion Cyclotron Resonance ("FTICR") mass analyzer; (ix) an electrostatic or orbitrap mass analyzer; (x) a Fourier Transform electrostatic or orbitrap mass analyzer; (xi) a Fourier Transform mass analyzer; (xii) a Time of Flight mass analyzer; (xiii) an orthogonal acceleration Time of Flight mass analyzer; and (xiv) a linear acceleration Time of Flight mass analyzer; and/or (h) one or more energy analyzers or electrostatic energy analyzers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wein filter; and/or (k) a device or ion gate for pulsing ions; and/or (l) a device for converting a substantially continuous ion beam into a pulsed ion beam.

The mass spectrometer may further comprise either:

(i) a C-trap and an Orbitrap® mass analyzer comprising an outer barrel-like electrode and a coaxial inner spindle-like electrode, wherein in a first mode of operation ions are transmitted to the C-trap and are then injected into the Orbitrap® mass analyzer and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the Orbitrap® mass analyzer; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The present invention is directed to increasing the performance of a mass spectrometer performing Data Directed Acquisitions or experiments (DDA) by reducing the processing requirements and enhancing the optimisation of fragmenting or reacting ions. The desire to increase the performance or duty cycle of mass spectrometers performing Data Directed Analysis ("DDA") places increased requirements on the mass spectrometer in terms of the time taken to process the initial survey spectrum. As the processing becomes more complex and includes some chemical intelligence then it is particularly important to minimise the additional processing requirements or overheads. The present invention processes a DDA survey spectrum so as to determine the charge state of parent ions of interest based upon the mass to charge ratio and the ion mobility drift time of the ions, and then preferably uses this information to set the appropriate collision energy or otherwise optimise a fragmentation or reaction condition based upon this information.

BRIEF DESCRIPTION OF THE DRAWINGS

Various embodiments of the present invention will now be described together with an arrangement given for illustrative purposes only, by way of example only, and with reference to the accompanying drawings in which.

DETAILED DESCRIPTION OF PREFERRED EMBODIMENTS

Figure 1:
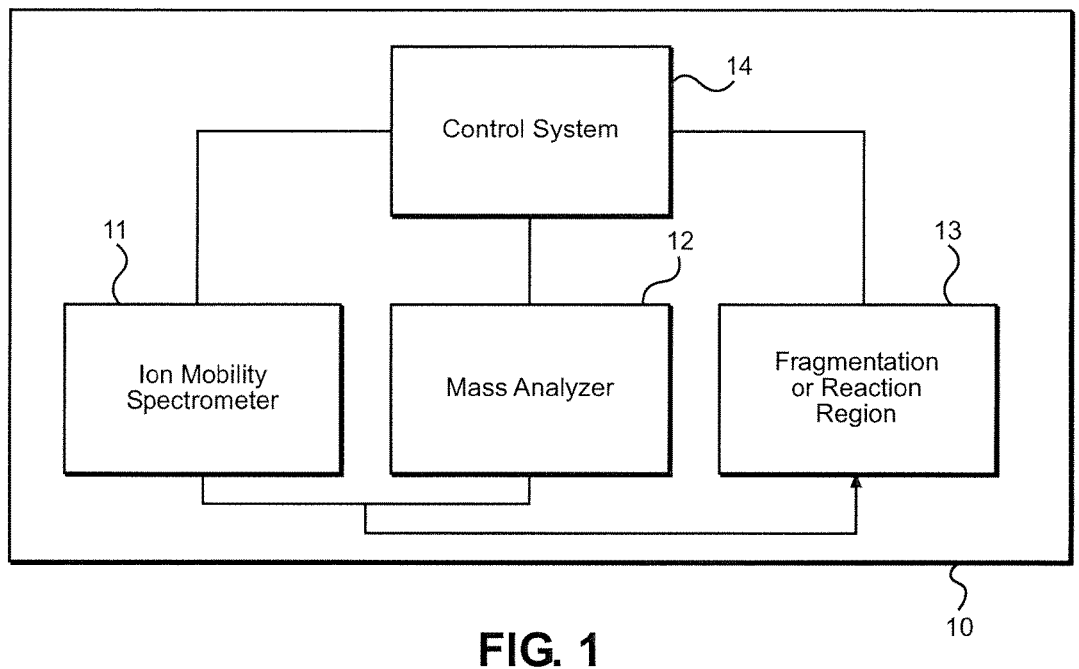
FIG. 1 shows a mass spectrometer according to an embodiment of the present invention.

A mass spectrometer according to an embodiment the present invention is shown in FIG. 1. A mass spectrometer 10 comprises: an ion mobility spectrometer 11; a mass analyzer 12; a fragmentation or reaction region 13; and a control system 14 arranged and adapted to:

perform a survey scan of a plurality of different types of parent or precursor ions, wherein said survey scan comprises analyzing the ion mobilities of the ions in said ion mobility spectrometer and mass analyzing the ions in said mass analyzer;

determine the charge states of the parent or precursor ions analyzed in the survey scan based on their determined combinations of ion mobility and mass to charge ratio;

select a parent or precursor ion for fragmentation or reaction in said fragmentation or reaction region;

select the fragmentation or reaction condition from a plurality of fragmentation or reaction conditions based upon the determined charge state of the selected ion; and fragment or react said selected ion under said selected fragmentation or reaction condition in said fragmentation or reaction region.

Figure 2:
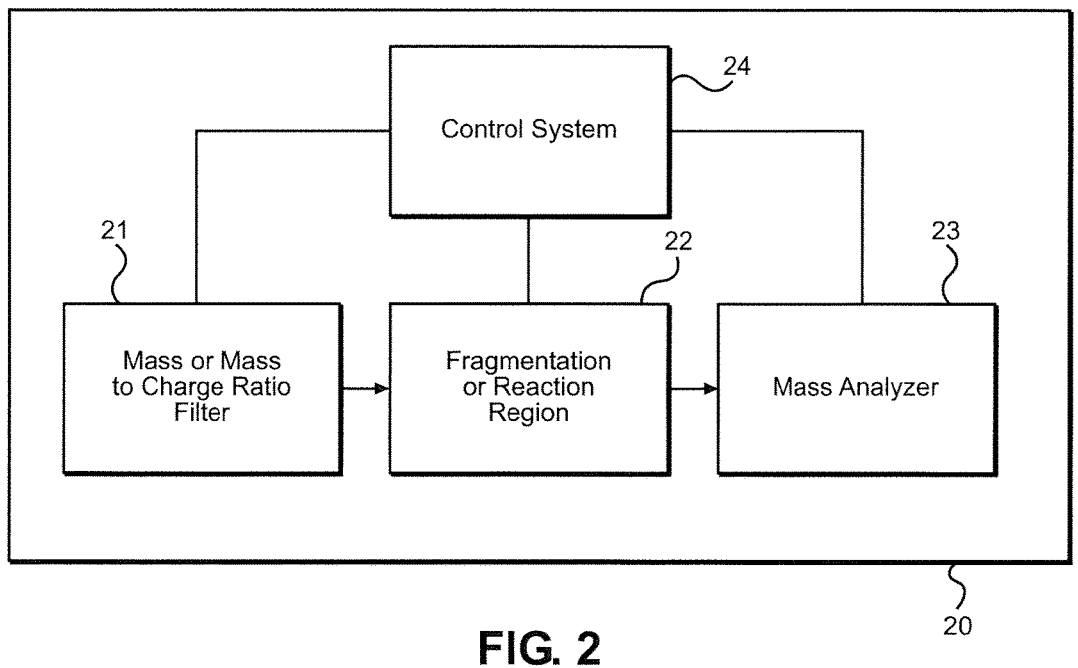
FIG. 2 shows a mass spectrometer according to another embodiment of the present invention.

A mass spectrometer according to another embodiment the present invention is shown in FIG. 2. A mass spectrometer 20 comprises: a mass or mass to charge ratio filter 21; a fragmentation or reaction region 22; a mass analyzer 23; and a control system 24 arranged and adapted to:

(i) to perform an initial survey scan;

(ii) to determine the charge state of at least some ions of interest;

(iii) to determine or select one or more fragmentation or reaction conditions for said ions of interest based upon the determined charge state of said ions of interest;

(iv) to select at least some of said ions of interest using said mass or mass to charge ratio filter;

(v) to cause said selected ions of interest to fragment or react under said one or more fragmentation or reaction conditions in said fragmentation or reaction device so as to form fragment or product ions; and then (vi) to mass analyze said fragment or product ions using said mass analyzer.

The preferred embodiment of the present invention relates to a DDA experiment wherein, in the MS mode of operation, the precursor or parent ions are separated by ion mobility in an ion mobility separator and are then mass analyzed by a mass analyzer. The knowledge of the drift time through the ion mobility separator (IMS) provides an indication of the ion mobility of an ion. This, together with the mass to charge ratio of the ion, is used to determine or estimate the charge state of candidate parent or precursor ions. The charge state of the ions may then be used to either include parent or precursor ions or reject parent or precursor ions from subsequent MS/MS experiments.

The charge states determined for the parent or precursor ions that are selected for the subsequent MS/MS experiments may then be used to set an appropriate collision energy (or one or more other fragmentation conditions). This removes the need to de-isotope the survey spectra and also reduces the processing of the survey spectra that is required, hence reducing the dead time of the instrument.

Rather than using the determined charge state to set an appropriate collision energy, the determined charge state of the candidate parent or precursor ions may be used to determine the fragmentation methodology employed in the MS/MS modes. For example, depending on the charge state that has been determined, the candidate ion may be fragmented using either Electron Transfer Dissociation ("ETD") or Collision Induced Dissociation ("CID"). Relatively high charge state candidate ions may be fragmented using ETD conditions, whereas relatively low charge state candidate ion may be fragmented using CID conditions. The fragmentation may therefore be optimised for the different types of ions.

To reduce processing requirements, mass spectral data may be discarded for parent or precursor ions that have charge states or information that is not of particular interest. For example, the IMS drift time and preferably mass to charge ratio may be used to identify and select just a certain class of compounds for MS/MS analysis. Examples of such classes of compound include lipids or glycans, polymers such as PEG or PPG, or pharmaceuticals containing active ingredients that are reacted with polymers such as PEG to increase their "lifetime" in the body. Compounds may also be selected if they fall upon or within a given or known drift time-mass to charge ratio trend line and select the appropriate collision energy for the mass to charge ratio within that class.

An exemplary embodiment of the present invention comprises an ion source, an ion mobility separator (IMS), a collision cell and a mass analyzer. In operation, parent or precursor ions are generated by the ion source and a survey scan is performed on these ions. The ions are directed into the IMS device and ions having different mobilities pass through the gas in the IMS device with different drift times. The IMS device therefore causes the ions to separate according to their ion mobility through the IMS device. The ions then pass to a mass analyzer, which determines the mass to charge ratios of the ions as a function of their IMS drift times or ion mobilities. The charge state of any given parent or precursor ion is determined from its combination of ion mobility and mass to charge ratio.

Ions having desired combinations of mass to charge ratio and ion mobility (i.e. charge state) are then selected for MS/MS analysis. In the MS/MS mode, the parent or precursor ions are passed through the IMS device and a mass filter, which are operated so as to only transmit ions of interest that have the desired a combination of mass to charge ratio and ion mobility. These ions are then fragmented in the collision cell. The fragmentation conditions for fragmenting the parent or precursor ions may be selected based on the combination of ion mobility and mass to charge ratio of the ions of interest (i.e. based on the charge state). The resulting fragment ions are then mass analyzed and may be correlated with their respective parent or precursor ions. The MS/MS process may then be repeated for a different precursor or parent ion of interest by setting the IMS device and mass filter to transmit said different precursor or parent ion of interest to the collision cell.

Different ions belonging to the same chemical class of compounds tend to have mass to charge ratios and ion mobilities that follow a common trend. If it is desired to investigate only ions in such a class of compounds then only the parent or precursor ions that follow the trend are selected for the MS/MS analysis.

Although the present invention has been described with reference to preferred embodiments, it will be understood by those skilled in the art that various changes in form and detail may be made without departing from the scope of the invention as set forth in the accompanying claims.

The invention claimed is:

1. A method of mass spectrometry comprising:
performing a survey scan of a plurality of different types of parent or precursor ions, wherein said survey scan comprises analyzing ion mobilities of the ions and mass analyzing the ions;
determining charge states of parent or precursor ions analyzed in the survey scan based on their determined combinations of ion mobility and mass to charge ratio;
selecting a parent or precursor ion for fragmentation or reaction; and
fragmenting or reacting said selected ion, wherein the fragmentation or reaction conditions are selected from a plurality of different fragmentation or reaction conditions based upon the determined charge state of the selected ion.

2. The method of claim 1, wherein the method of mass spectrometry is a method of data dependent acquisition (DDA) mass spectrometry.

3. The method of claim 1, wherein said step of selecting a parent or precursor ion for fragmentation or reaction comprises selecting a parent or precursor ion based on its determined charge state.

4. The method of claim 1, comprising sequentially selecting and fragmenting or reacting different parent or precursor ions.

5. The method of claim 1, wherein any given selected ion is isolated from other ions before being subjected to said fragmentation or reaction.

6. The method of claim 1, comprising selecting an optimum fragmentation or reaction condition for the selected ion based upon the determined charge state of the ion; or
wherein the step of fragmenting or reacting said ion comprises fragmenting said ion, and wherein a fragmentation energy with which the ion is fragmented is selected based upon the determined charge state of the selected ion.

7. The method of claim 1, wherein the step of fragmenting or reacting the ion comprises fragmenting said ions by Collision Induced Dissociation ("CID"), and wherein a collision energy is selected based upon the determined charge state of the selected ion.

8. The method of claim 1, comprising providing means for fragmenting or reacting said ions by a plurality of different fragmentation or reaction techniques, wherein said step of selecting the fragmentation or reaction condition comprises selecting between said plurality of different types of fragmentation or reaction techniques based upon the determined charge state of the selected ion, and then fragmenting or reacting the selected ion using the selected fragmentation or reaction technique.

9. The method of claim 1, wherein a collision energy or fragmentation condition is selected based upon the determined charge state of the parent or precursor ion and also based upon a determined mass to charge ratio value of the parent or precursor ion.

10. The method of claim 1, comprising mass analyzing or ion mobility analyzing the fragment or product ions resulting from said fragmenting or reacting step.

11. The method of claim 10, comprising associating the fragment or product ions with their respective parent or precursor ions.

12. The method of claim 10, comprising identifying one or more parent or precursor ions using said analyzed product or fragment ions.

13. A mass spectrometer comprising:
an ion mobility spectrometer;
a mass analyzer;
a fragmentation or reaction region; and
a control system arranged and adapted to:
perform a survey scan of a plurality of different types of parent or precursor ions, wherein said survey scan comprises analyzing the ion mobilities of the ions in said ion mobility spectrometer and mass analyzing the ions in said mass analyzer;
determine charge states of the parent or precursor ions analyzed in the survey scan based on their determined combinations of ion mobility and mass to charge ratio;
select a parent or precursor ion for fragmentation or reaction in said fragmentation or reaction region;
select the fragmentation or reaction condition from a plurality of fragmentation or reaction conditions based upon the determined charge state of the selected ion; and
fragment or react said selected ion under said selected fragmentation or reaction condition in said fragmentation or reaction region.

14. The mass spectrometer of claim 13, wherein the mass spectrometer is arranged and adapted to perform a method of data dependent acquisition (DDA) mass spectrometry.

15. A method of mass spectrometry comprising:
separating ions according to their ion mobility;
mass analyzing said ions;
determining the charge state of at least some of said ions based upon the determined ion mobility and mass to charge ratio of said ions; and
determining or selecting one or more fragmentation or reaction conditions for said ions based upon the determined charge state of said ions.

16. A method as claimed in claim 15, further comprising:
arranging a fragmentation or reaction device to operate under said one or more fragmentation or reaction conditions; and fragmenting or reacting ions in said fragmentation or reaction device.

17. A method as claimed in claim 16, wherein the step of fragmenting or reacting said ions comprises fragmenting said ions in a Collision Induced Dissociation ("CID") fragmentation device.

18. A method as claimed in claim 15, wherein the step of determining or selecting said one or more fragmentation or reaction conditions comprises determining or selecting an optimum collision energy for said ions.

19. A method as claimed in claim 15, wherein the step of determining or selecting said one or more fragmentation or reaction conditions comprises determining whether or not to fragment or react said ions by Collision Induced Dissociation ("CID") or by Electron Transfer Dissociation ("ETD").

20. A mass spectrometer comprising:
an ion mobility spectrometer;
a mass analyzer; and
a control system arranged and adapted:
(i) to determine the charge state of at least some ions based upon determining the ion mobility and mass to charge ratio of said ions; and
(ii) to select or determine one or more fragmentation or reaction conditions for said ions based upon the determined charge state of said ions.

21. A mass spectrometer as claimed in claim 20, further comprising a fragmentation or reaction device.

22. A mass spectrometer as claimed in claim 21, wherein said control system is further arranged and adapted:
(i) to cause said fragmentation or reaction device to operate under said one or more fragmentation or reaction conditions; and
(ii) to cause said ions to be fragmented or reacted in said fragmentation or reaction device.

23. A method of mass spectrometry comprising:
performing an initial survey scan;
determining the charge state of at least some ions of interest by determining an ion mobility drift time and mass to charge ratio of said ions of interest;
determining or selecting one or more fragmentation or reaction conditions for said ions of interest based upon the determined charge state of said ions of interest;
selecting at least some of said ions of interest;
causing said selected ions of interest to fragment or react under said one or more fragmentation or reaction conditions so as to form fragment or product ions; and then
mass analyzing said fragment or product ions.

24. A method as claimed in claim 23, wherein the step of determining or selecting said one or more fragmentation or reaction conditions for said ions of interest comprises determining an optimum electric field to be maintained upstream of a Collision Induced Dissociation ("CID") fragmentation device so that said ions of interest are accelerated into said Collision Induced Dissociation fragmentation device with an optimal collision energy for fragmentation.

25. A mass spectrometer comprising:
a mass or mass to charge ratio filter;
a fragmentation or reaction device;
a mass analyzer; and a control system arranged and adapted:
(i) to perform an initial survey scan;
(ii) to determine the charge state of at least some ions of interest by determining an ion mobility drift time and mass to charge ratio of said ions of interest;
(iii) to determine or select one or more fragmentation or reaction conditions for said ions of interest based upon the determined charge state of said ions of interest;
(iv) to select at least some of said ions of interest using said mass or mass to charge ratio filter;
(v) to cause said selected ions of interest to fragment or react under said one or more fragmentation or reaction conditions in said fragmentation or reaction device so as to form fragment or product ions; and then
(vi) to mass analyze said fragment or product ions using said mass analyzer.

* * * * *